(12) United States Patent
Nishimura

(10) Patent No.: US 11,556,731 B2
(45) Date of Patent: Jan. 17, 2023

(54) ENDOSCOPIC IMAGE OBSERVATION SYSTEM, ENDOSIPIC IMAGE OBSERVATION DEVICE, AND ENDOSCOPIC IMAGE OBSERVATION METHOD

(71) Applicant: OLYMPUS CORPORATION, Tokyo (JP)

(72) Inventor: Norio Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 442 days.

(21) Appl. No.: 16/672,635

(22) Filed: Nov. 4, 2019

(65) Prior Publication Data
US 2020/0065614 A1 Feb. 27, 2020

Related U.S. Application Data

(63) Continuation of application No. PCT/JP2018/021598, filed on Jun. 5, 2018.

(30) Foreign Application Priority Data

Sep. 29, 2017 (JP) .............................. JP2017-191730

(51) Int. Cl.
*G06K 9/62* (2022.01)
*A61B 1/00* (2006.01)
(Continued)

(52) U.S. Cl.
CPC .......... *G06K 9/6218* (2013.01); *A61B 1/0005* (2013.01); *A61B 1/041* (2013.01); *G06V 10/22* (2022.01); *G06V 2201/031* (2022.01)

(58) Field of Classification Search
CPC .. G06K 9/6218; G06K 9/2054; G06K 9/6223; G06K 2209/051; A61B 1/0005; A61B 1/041; A61B 1/00009
See application file for complete search history.

(56) References Cited

U.S. PATENT DOCUMENTS 8,873,816 B1 * 10/2014 Peleg .................. G06V 20/698
382/128
8,929,629 B1 * 1/2015 Rozenfeld ............ A61B 5/7275
382/128

(Continued)

FOREIGN PATENT DOCUMENTS

EP          2412300 B1 *  3/2014 .......... G06T 7/0002
JP       2004-321603 A    11/2004
(Continued)

OTHER PUBLICATIONS

International Preliminary Report on Patentability dated Mar. 31, 2020, together with the Written Opinion received in related International Application No. PCT/JP2018/021598.

(Continued)

*Primary Examiner* — Matthew C Bella
*Assistant Examiner* — Kathleen M Broughton
(74) *Attorney, Agent, or Firm* — Scully, Scott, Murphy & Presser, P.C.

(57) ABSTRACT

An endoscopic image observation system supports the observation of a plurality of images captured by a capsule endoscope. The endoscopic image observation system includes a distinguishing unit that outputs an accuracy score indicating the likelihood that each of the plurality of images represents an image of a region sought to be distinguished; a grouping unit that groups the plurality of images into a plurality of clusters in accordance with the accuracy score; and an identification unit that identifies a candidate image for a boundary of the region from among the plurality of images in accordance with the grouping into the plurality of clusters.

8 Claims, 14 Drawing Sheets

(51) Int. Cl.
    *A61B 1/04*    (2006.01)
    *G06V 10/22*   (2022.01)

(56) References Cited

U.S. PATENT DOCUMENTS

| | | |
|---|---|---|
| 2004/0225223 A1 | 11/2004 | Honda et al. |
| 2011/0032259 A1 | 2/2011 | Kim et al. |
| 2011/0206250 A1* | 8/2011 | McGinnis ............. G06T 7/0012 |
| | | 382/128 |
| 2011/0255759 A1* | 10/2011 | Nishimura ......... A61B 1/00016 |
| | | 382/128 |
| 2012/0274743 A1 | 11/2012 | Takasugi et al. |
| 2012/0316421 A1* | 12/2012 | Kumar ............... A61B 1/00009 |
| | | 600/407 |
| 2013/0152020 A1 | 6/2013 | Nishiyama |
| 2016/0292875 A1* | 10/2016 | Kono .................... G06T 7/0012 |
| 2017/0296043 A1 | 10/2017 | On |

FOREIGN PATENT DOCUMENTS

| | | | | |
|---|---|---|---|---|
| JP | 2015-112431 A | 6/2015 | | |
| WO | WO-2012039171 A1 * | 3/2012 | ......... | A61B 1/00016 |
| WO | 2012/063623 A1 | 5/2012 | | |
| WO | 2016-110993 A1 | 7/2016 | | |
| WO | WO-2017027475 A1 * | 2/2017 | ........... | G06K 9/6255 |
| WO | WO-2017055412 A1 * | 4/2017 | ......... | G06K 9/00147 |

OTHER PUBLICATIONS

International Search Report dated Jul. 17, 2018 issued in International Application No. PCT/JP2018/021598.

* cited by examiner

ENDOSCOPIC IMAGE OBSERVATION SYSTEM, ENDOSOPIC IMAGE OBSERVATION DEVICE, AND ENDOSCOPIC IMAGE OBSERVATION METHOD

CROSS-REFERENCE TO RELATED APPLICATIONS

This application is based upon and claims the benefit of priority from the prior Japanese Patent Applications No. 2017-191730, filed on Sep. 29, 2017, and International Application No. PCT/JP2018/021598, filed on Jun. 5, 2018, the entire contents of which are incorporated herein by reference.

BACKGROUND OF THE INVENTION

1. Field of the Invention

The present invention relates to an endoscopic image observation system.

2. Description of the Related Art

Japanese Patent Application Publication No. 2004-321603 discloses grouping in-vivo image data acquired by a capsule endoscope for each predetermined region in the inside of a subject.

In capsule endoscopic examination, tens of thousands of images are captured. The image interpreter observes played back and displayed endoscopic images and extracts images that contain abnormal findings. However, since the number of images is enormous, the burden of image interpretation is significant. In a device described in Japanese Patent Application Publication No. 2004-321603, for the purpose of improving the efficiency of image observation and reducing the burden of image interpretation, the ranges of regions, in other words, the boundaries of the regions are automatically distinguished based on the color of the image, and the result of automatic distinction is displayed along with a bar showing the color of the image in chronological order. Since the result of the automatic distinction includes errors, it is necessary to search for the actual boundaries of the regions with reference to the result of the automatic distinction. Since it is unclear an image of which chronological order range should be searched for, the searching task takes time and effort.

SUMMARY OF THE INVENTION

In this background, a purpose of the present invention is to provide a technique that allows an image interpreter to be able to easily find an image of a boundary of a region.

An observation system according to one embodiment of the present invention is an observation system for supporting observation of a plurality of images captured by a capsule endoscope comprising a processor comprising hardware, wherein the processor is configured to: output an accuracy score indicating a likelihood that each of the plurality of images represents an image of a region sought to be distinguished; group the plurality of images into a plurality of clusters in accordance with the accuracy score; and identify a candidate image for a boundary of the region from among the plurality of images in accordance with the grouping into the plurality of clusters.

Another embodiment of the present invention relates to an observation device. The device comprises a processor comprising hardware, wherein the processor is configured to, wherein a plurality of images captured by a capsule endoscope are grouped into a plurality of clusters based on an accuracy score that has been output for each of the plurality of images indicating the likelihood that the image represents an image of a region sought to be distinguished, display, on a display, information regarding a candidate image for a boundary of the region extracted from among the plurality of images in accordance with the grouping into the plurality of clusters.

Still another embodiment of the present invention also relates to an observation device. The device comprises a processor comprising hardware, wherein the processor is configured to, wherein a plurality of images captured by a capsule endoscope are grouped into a plurality of clusters based on an accuracy score that has been output for each of the plurality of images indicating the likelihood that the image represents an image of a region sought to be distinguished, identify a candidate image for a boundary of the region from among the plurality of images in accordance with the grouping into the plurality of clusters in order to display on a display.

Still another embodiment of the present invention relates to an observation method. The method includes: outputting an accuracy score indicating the likelihood that each of a plurality of images captured by a capsule endoscope represents an image of a region sought to be distinguished; grouping the plurality of images into a plurality of clusters in accordance with the accuracy score; and identifying a candidate image for a boundary of the region from among the plurality of images in accordance with the grouping into the plurality of clusters.

Optional combinations of the aforementioned constituting elements and implementations of the invention in the form of methods, apparatuses, systems, recording mediums, and computer programs may also be practiced as additional modes of the present invention.

BRIEF DESCRIPTION OF THE DRAWINGS

Embodiments will now be described, by way of example only, with reference to the accompanying drawings that are meant to be exemplary, not limiting, and wherein like elements are numbered alike in several figures, in which.

DETAILED DESCRIPTION OF THE INVENTION

Figure 1:
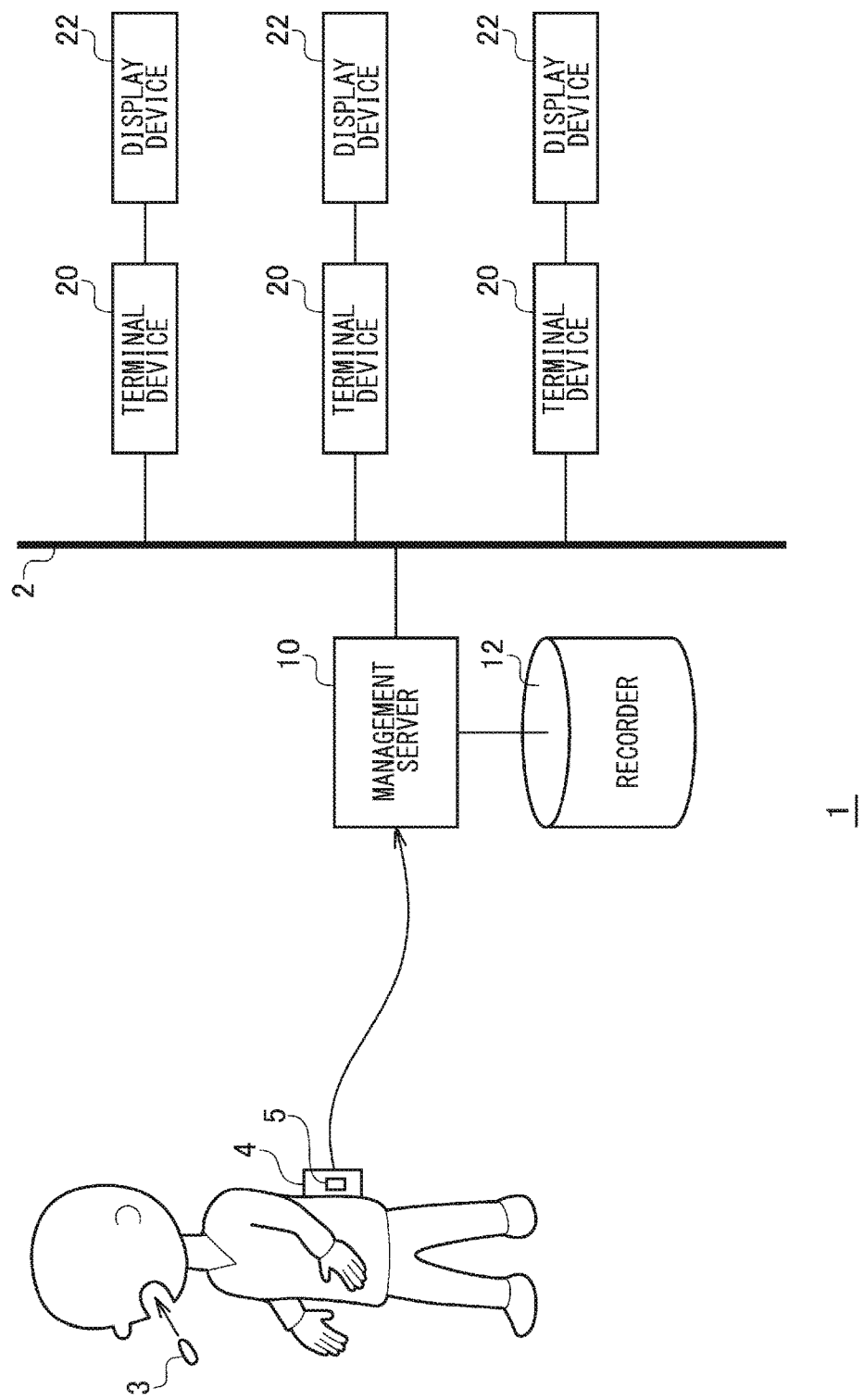
FIG. 1 is a diagram for explaining the outline of an image observation system according to a first embodiment.

The invention will now be described by reference to the preferred embodiments. This does not intend to limit the scope of the present invention, but to exemplify the invention.

A description will be given of the present invention with reference to the drawings based on preferred embodiments. The same or equivalent constituting elements, members, and processes illustrated in each drawing shall be denoted by the same reference numerals, and duplicative explanations will be omitted appropriately. Further, the embodiments do not limit the invention and are shown for illustrative purposes, and all the features described in the embodiments and combinations thereof are not necessarily essential to the invention.

First Embodiment

FIG. 1 is a diagram for explaining the outline of an image observation system of a capsule endoscope according to a first embodiment. An endoscopic image observation system 1 supports observation of a capsule endoscopic image by an image interpreter. In an examination where a usual endoscope is used, a doctor observes an image captured by an endoscope inserted in a patient's body in real time on a display and makes a diagnosis. However, a capsule endoscopic examination is different from a usual endoscopic examination in that the image interpreter collectively observes a large amount of images captured in the past by a capsule endoscope.

In a capsule endoscopic examination, the patient swallows a capsule endoscope 3 having a built-in ultracompact camera from the mouth, with a plurality of antennas (not shown) being attached to the abdomen and a receiver 4 being attached to the waist by a belt. The capsule endoscope 3 captures a still image periodically as the capsule endoscope 3 moves through the digestive tract and transmits to the receiver 4 via the antennas an image file obtained by adding an image ID and imaging time information to a captured image. The capsule endoscope 3 according to the present embodiment has a function of changing an imaging frame rate and may capture images, for example, by increasing the imaging frame rate when the movement speed increases.

A recording medium 5 is built in the receiver 4, and the receiver 4 records a received image file in the recording medium 5. In the case where the capsule endoscope 3 images the inside of the body every 0.5 seconds, about 60,000 endoscopic image files are recorded in the recording medium 5 when the imaging of the inside of the body is completed in about 8 hours.

The image ID is information for identifying the image and may be information to which a serial number indicating the imaging order is assigned. For example, "1" may be assigned to the image ID of an endoscopic image captured first, and "2" may be assigned to the image ID of an endoscopic image captured second. Generating an image ID in this manner allows a serial number included in the image ID to represent the order of capturing images and duplication of image IDs to be avoided. The image ID and the imaging time information may be added to the captured image by the receiver 4 when the receiver 4 receives the captured image. In any case, the image captured by the capsule endoscope 3 is recorded in the recording medium 5 in association with the image ID and imaging time information.

When the antennas and the receiver 4 are collected from the patient, a data terminal of the receiver 4 becomes connected to a data reader connected to a management server 10, and the data reader reads about 60,000 endoscopic image files recorded in the recording medium 5 and transmits the endoscopic image files to the management server 10. The data reader may be an external device that becomes connected to the management server 10 by a USB cable or the like. The recording medium 5 may be a memory card detachable from the receiver 4, and the recording medium 5 may be removed from the receiver 4 and installed in the data reader such that the endoscopic image files are read out. The recording medium 5 may be inserted in a data reading slot provided in the management server 10 such that the endoscopic image files are read out.

The management server 10 performs a predetermined image process on endoscopic images read from the recording medium 5 and records the images in the recorder 12. The recorder 12 may be comprised of a hard disk drive (HDD) or a flash memory. Since the endoscopic images recorded in the recording medium 5 are uncompressed RAW (raw) images or RAW images on which only lossless compression has been performed, the data size thereof is very large. Therefore, the management server 10 performs a predetermined lossy compression process on the endoscopic images that are RAW images so as to reduce the data size thereof and records the images in the recorder 12. In this embodiment, the management server 10 is in charge of an image process on endoscopic RAW images. However, another device, for example, a terminal device 20 may perform the image process on the endoscopic RAW images and records the images in the recorder 12, and the recorder 12 may be provided in the terminal device 20.

A plurality of terminal devices 20 are connected to the management server 10 via a network 2 such as a local area network (LAN). For example, the terminal devices 20 are personal computers assigned to doctors and/or technicians (hereinafter may be simply referred to as "user(s)") and are connected to display devices 22 to allow an output to be displayed on the respective screens. The terminal devices 20 may be laptop computers integrated with a display device or portable tablets. The terminal devices 20 access the management server 10 to display the endoscopic images recorded in the recorder 12 on the display devices 22.

The management server 10 has a function of executing, when compressing an endoscopic RAW image, an analysis application and analyzing the endoscopic image. Image analysis by the analysis application is performed on all endoscopic RAW images captured in one capsule endoscopic examination, and the result of the image analysis is added as additional information to the compressed endoscopic images.

One of the purposes of a capsule endoscopic examination is to find the source of bleeding in a digestive tract. Upon acquiring the endoscopic RAW images from the recording medium 5, the management server 10 executes the analysis application so as to perform the image process, thereby identifying an endoscope RAW image in which a bleeding state may have been captured. For example, when the redness in an endoscopic image exceeds a predetermined threshold value, the management server 10 determines that the image is likely to be an image in which a bleeding condition has been captured and adds flag information indicating that the image is a reddish image when compressing the endoscopic RAW image.

The moving speed of the capsule endoscope 3 in a digestive tract varies depending on the location. Where the moving speed is low, the variation between endoscopic images captured is small. Therefore, it is inefficient and burdensome for an image interpreter to equally observe all the endoscopic images including a plurality of endoscopic images with almost no change. In this background, the analysis application compares endoscopic RAW images captured successively in time and performs a process of identifying an image with small change (similar image). Hereinafter, this process will be referred to as "image summarization process".

In the image summarization process, a reference image is set, and the ratio of a coverage area of the reference image occupying a determination target image subjected to determination as to whether or not the image is similar to the reference image is calculated as a coverage rate. The determination target image is an image captured after the reference image. When the coverage rate is equal to or greater than a threshold value, the analysis application determines the determination target image as a similar image of the reference image. When compressing an endoscopic RAW image serving as the reference image, the management server 10 adds flag information indicating that the image is a reference image, and when compressing an endoscopic RAW image that is a similar image, the management server 10 adds flag information indicating that the image is a similar image.

Further, from among a plurality of reference images, the analysis application identifies a candidate image in which the boundary of a region in the body may have been captured. When an image interpreter makes a diagnosis using a predetermined region as a main target, the image interpreter is preferably able to easily recognize which captured endoscopic images are images that have captured the target region. Since the capsule endoscope 3 images the inside of each of digestive tract parts: "stomach"; "small intestine"; and "large intestine", by identifying, in advance by the analysis application, a candidate image in which the entrance (start position) of each of the digestive tract parts may have been captured, the image interpreter can easily find the boundary of each of the digestive tract parts at the time of image diagnosis.

A playback application executed in the management server 10 or the terminal device 20 has a playback mode for shortening the playback time of endoscope images with reference to flag information added in the image summarization process. By selecting this playback mode, the image interpreter allows for the shortening of the observation time.

The playback application according to the embodiment has four playback modes.

(First Playback Mode)

The first playback mode is a manual playback mode using the operation of a user interface connected to the terminal device 20. In the first playback mode, the user rotates the wheel of a mouse wheel so that the endoscopic images can be frame-by-frame displayed one by one. Therefore, the first playback mode is used for identifying an image in which a pathological change has been captured most distinctly from among a plurality of images in which the pathological change has been captured. When the user rotates the wheel in a direction away from the user, the endoscopic images are continuously played back and displayed in the forward direction (a direction moving from an image with an old imaging time toward a new image), and when the user rotates the wheel in a direction toward the user, the endoscopic images are continuously played back and displayed in the backward direction (a direction moving from an image with a new imaging time toward an old image).

(Second Playback Mode)

The second playback mode is an automatic playback mode in which the endoscopic images are continuously played back and displayed in the forward direction or the backward direction at a playback speed that has been set. The second playback mode is used for normal endoscopic image observation.

(Third Playback Mode)

The third playback mode is an automatic playback mode in which, while reference images identified through the image summarization process are continuously played back and displayed in the forward direction or the backward direction at a playback speed that has been set, similar images are continuously played back and displayed in the forward direction or the backward direction at a speed higher than the playback speed that has been set. In the third playback mode, by playing back the similar images having a small change from the reference images at a high speed, the shortening of the observation time as compared with the second playback mode can be realized.

(Fourth Playback Mode)

The fourth playback mode is an automatic playback mode in which, while the display of the similar images identified through the image summarization process is omitted, only the reference images are played back and displayed in the forward direction or the backward direction at a playback speed that has been set. In the fourth playback mode, by omitting the display of the similar images, the shortening of the observation time as compared with the third playback mode can be realized. A secondary fourth playback mode, which is a secondary mode of the fourth playback mode may be set. The secondary fourth playback mode is an automatic playback mode in which, while the display of the reference images is omitted, only the similar images are played back and displayed in the forward direction or the backward direction at a playback speed that has been set. The secondary fourth playback mode is used to confirm that there is no omission in observation after the observation in the fourth playback mode.

The first to third playback modes are continuous playback modes for sequentially playing back and displaying endoscopic images that are sequential in time, and the fourth playback mode (the secondary fourth playback mode) is a decimating playback mode where temporally continuous endoscopic images are decimated so as to be played back and displayed. The playback application executes a playback process of the endoscopic images in accordance with a playback mode selected by the user. The playback application may be executed by the management server 10 or may be executed by the terminal device 20.

A user interface such as a keyboard, a mouse, etc., is connected to the terminal device 20. The terminal device 20 has a function of supporting an image interpretation task by the image interpreter in cooperation with the management server 10. The terminal device 20 causes the display device 22 to display an image interpretation screen for endoscope images, and the user observes the endoscopic images played back and displayed on the image interpretation screen and captures endoscopic images in which pathological changes, etc., have been captured.

Figure 2:
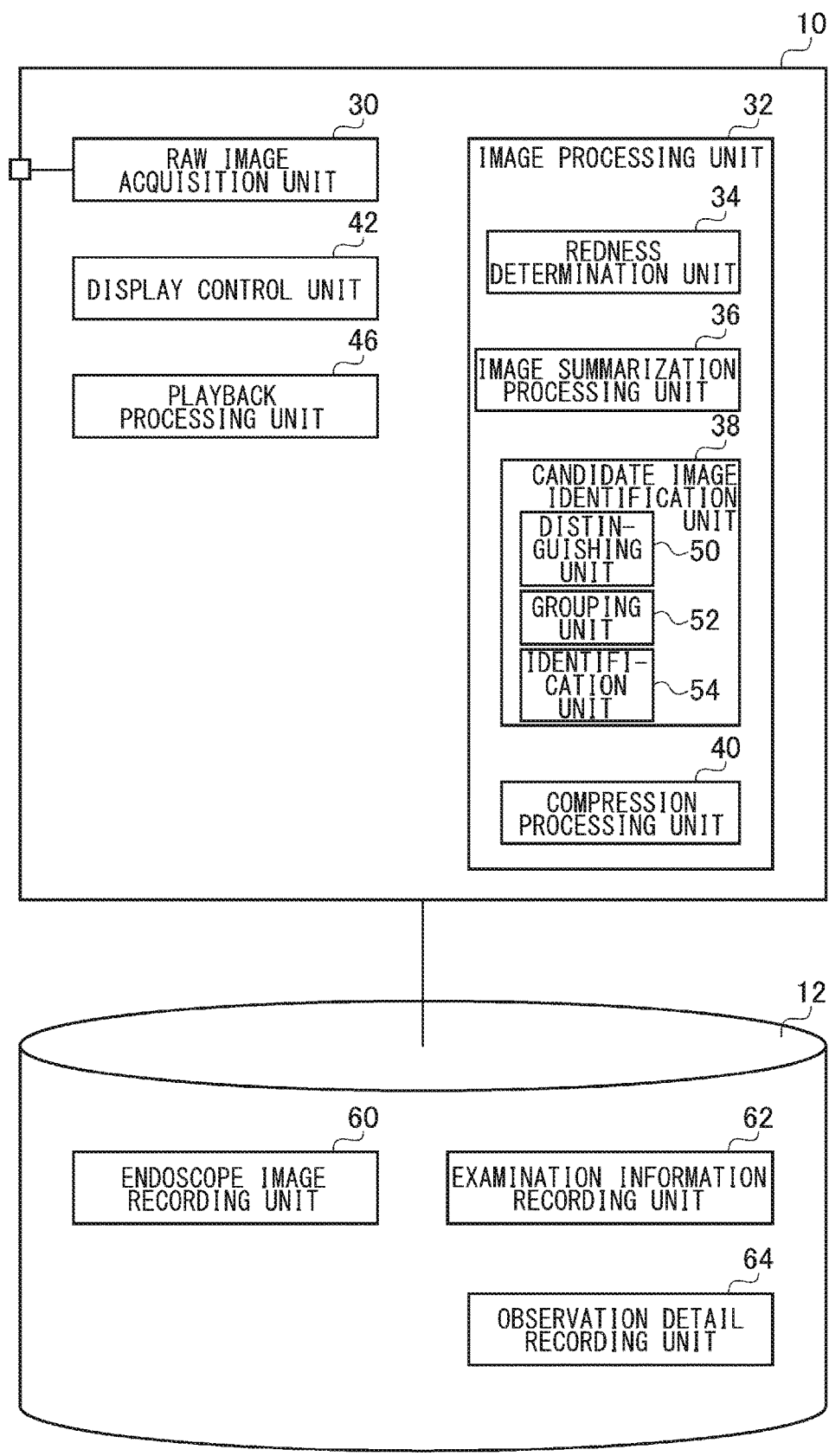
FIG. 2 is a diagram illustrating the configuration of a management server and a recorder in FIG. 1.

FIG. 2 shows the configuration of the management server 10 and the recorder 12. The management server 10 includes a RAW image acquisition unit 30, an image processing unit 32, a display control unit 42, and a playback processing unit 46. The image processing unit 32 has a redness determination unit 34, an image summarization processing unit 36, a candidate image identification unit 38, and a compression processing unit 40. The candidate image identification unit 38 has a distinguishing unit 50, a grouping unit 52, and an identification unit 54. Each function of the management server 10 may be realized by executing various applications such as an analysis application, a playback application, etc. In the embodiment, the management server 10 executes various applications. Alternatively, the terminal device 20 may execute various applications.

The recorder 12 includes an endoscope image recording unit 60, an examination information recording unit 62, and an observation detail recording unit 64. The endoscopic image recording unit 60 records an endoscopic image on which the image process has been performed by the image processing unit 32. The examination information recording unit 62 records information on an endoscopic examination. The observation detail recording unit 64 records the observation details of the endoscopic image, for example, images captured by the user, information on findings that has been input, and the like.

The configuration of the management server 10 is implemented by hardware such as a processor, a memory, or other LSIs and by software such as a program or the like loaded into the memory. The figure depicts functional blocks implemented by the cooperation of hardware and software. Thus, a person skilled in the art should appreciate that there are many ways of accomplishing these functional blocks in various forms in accordance with the components of hardware only, software only, or the combination of both.

The RAW image acquisition unit 30 acquires about 60,000 endoscope RAW images transmitted from the data reader and temporarily stores the images in the recorder 12. The image processing unit 32 performs the following image process on all the endoscope RAW images.

<Identification of Reddish Images>

The redness determination unit 34 searches for reddish endoscope RAW images by image analysis and identifies an image with redness that is stronger than a predetermined threshold value. The redness determination unit 34 provides the image ID of the identified reddish image to the compression processing unit 40.

<Image Summarization Process>

The image summarization processing unit 36 performs an image summarization process of grouping all the endoscopic images into reference images and similar images similar to the reference image. First, the image summarization processing unit 36 sets the first captured image as a reference image. The image summarization processing unit 36 performs similarity determination as to whether or not the determination target image captured next to the reference image is similar to the reference image. The image summarization processing unit 36 obtains a coverage area including a deformed image obtained by deforming the reference image in the determination target image and calculates, as a coverage rate, the ratio of the coverage area occupying the determination target image.

When the coverage rate is equal to or greater than a threshold value, the image summarization processing unit 36 determines the determination target image as a similar image of the reference image. The image summarization processing unit 36 performs, while using an image captured next to an image determined to be a similarity image, similarity determination as to whether or not the image is similar to the reference image. If the moving speed of the capsule endoscope 3 is slow, several tens of images captured after the reference image may be determined as similar images.

On the other hand, when the coverage rate is less than the threshold value, the image summarization processing unit 36 determines the determination target image as a non-similar image. The image summarization processing unit 36 sets an image determined to be a non-similar image as a new reference image and performs similarity determination using an image captured next to the image. The image summarization processing unit 36 performs this image summarization process on all the 60,000 or so endoscope RAW images and groups the images into reference images and similar images.

The ratio between the number of the reference images and the number of the similar images is adjusted by the setting of the threshold value. When the threshold value is increased, the number of reference images increases, and when the threshold value is decreased, the number of reference images decreases. In the fourth playback mode, since only reference images are played back and displayed, setting of the threshold value is important for suppressing overlooking of pathological changes and the like. Based on the past results, it has been found that the overlooking of images with pathological changes can be prevented through image interpretation of only the reference images by setting the threshold value such that about 20,000 endoscopic images out of about 60,000 endoscopic images are extracted as the reference images. The image summarization processing unit 36 provides the respective image IDs of the grouped reference images and the respective image IDs of the similar images each to the compression processing unit 40.

<Identification of Candidate Boundary Images>

Setting the position at which the boundary of a region inside the body has been captured as a landmark on a time bar allows the image interpreter to recognize the range of captured images for each region, which is convenient for making a diagnosis for an image of a specific region. The capsule endoscope 3 images the inside of each of the digestive tract parts: the stomach; the small intestine; and the large intestine. When the image interpreter observes only captured images of the small intestine, the range of captured images of the small intestine can be easily recognized by setting, as landmarks on the time bar, before image diagnosis both the position at which an image of the boundary between the stomach and the small intestine has been captured and the position at which an image of the boundary between the small intestine and the large intestine has been captured. Thus, the candidate image identification unit 38 performs a process of identifying a candidate image in which the boundary of a region inside the body may have been captured from among a plurality of endoscopic images before image observation by the image interpreter so that the image interpreter can easily find the boundary of the region inside the body.

Figure 3:
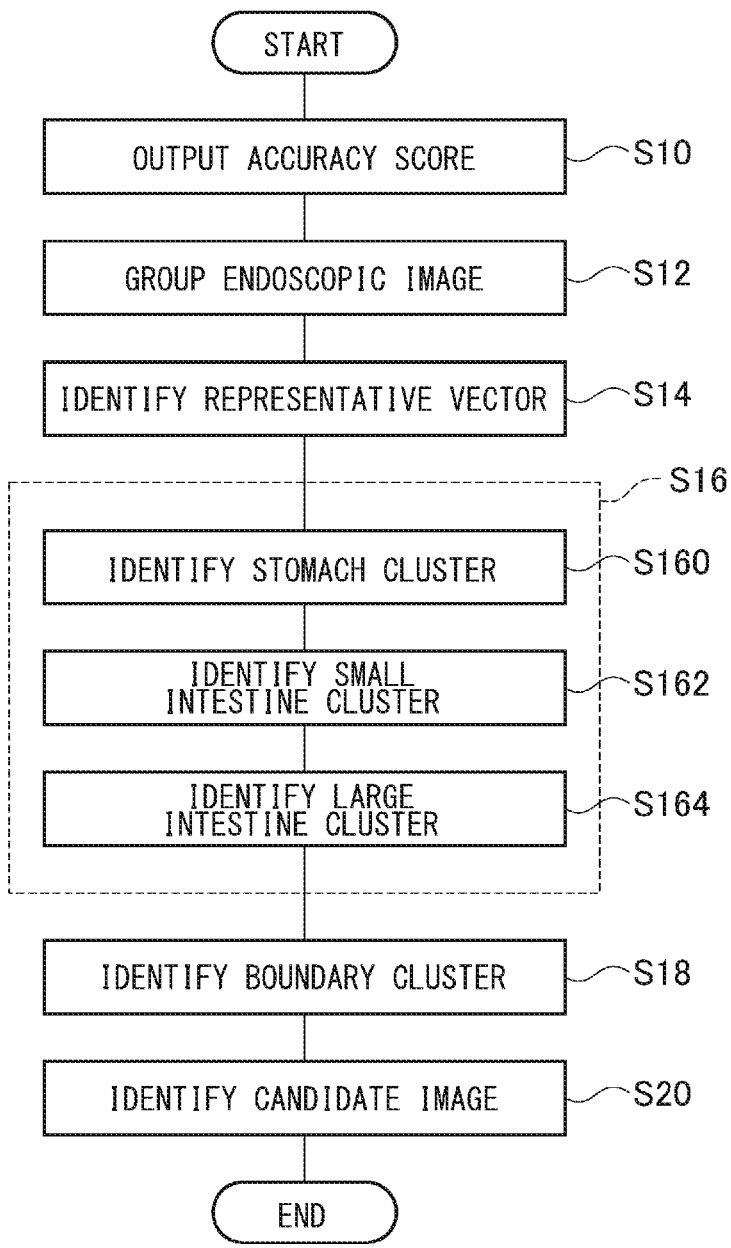
FIG. 3 is a diagram illustrating a flowchart of a candidate image identification process.

FIG. 3 shows a flowchart of a candidate image identification process. For all the endoscopic images, the distinguishing unit 50 outputs the likelihood (hereinafter, also referred to as "accuracy score") that each endoscopic image represents an endoscopic image of each region sought to be distinguished (S10). The process executed by the distinguishing unit 50 can be realized by using a known technique such as a machine learning technique such as SVM (Support Vector Machine), a neural network, or the like. In the present embodiment, each of the parts: the stomach; the small intestine; and the large intestine, represents a region sought to be distinguished, and the accuracy score is represented by a vector quantity expressed by the following equation. The likelihood represents a numerical value representing the degree of certainty of the distinction and is a real value between 0 and 1.

accuracy score=(likelihood for being an endoscopic image of the stomach, likelihood for being an endoscopic image of the small intestine, likelihood for being an endoscopic image of the large intestine)

The grouping unit 52 groups the plurality of endoscopic images into a plurality (K pieces) of clusters by a clustering method based on the accuracy score of each of the plurality of endoscopic images (S12). For this clustering, known techniques may be used. In the case of using a hierarchical method (e.g., the Ward method), K is applied as an initial value for the number of clusters to be grouped in the case where the merging of the clusters is stopped when the number of the clusters reaches K and a non-hierarchical method (e.g., K-means method) is used.

Figure 4:
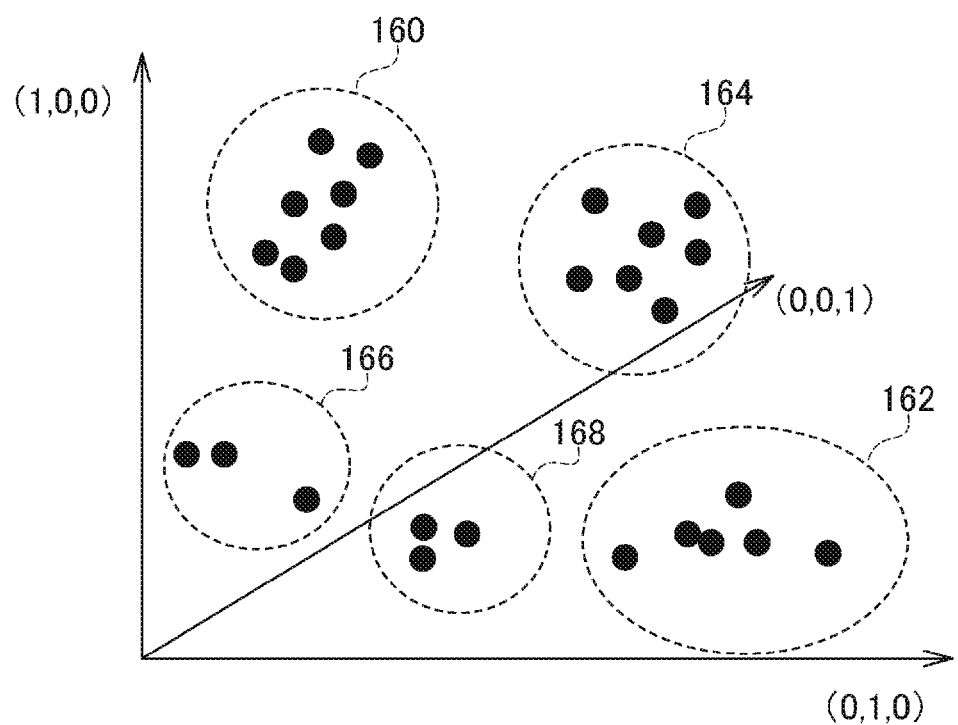
FIG. 4 is a diagram in which the respective accuracy scores of a plurality of endoscopic images are plotted in an orthogonal coordinate system.

FIG. 4 is a diagram in which the respective accuracy scores of a plurality of endoscopic images are plotted in an orthogonal coordinate system. Basically, as for the endoscopic images obtained by imaging the stomach, the likelihood of being endoscopic images of the stomach is determined to be high, and the likelihood of being endoscopic images of the small intestine or the large intestine is determined to be low. Thus, the endoscopic images concentrate near coordinates (1,0,0). Basically, as for endoscopic images obtained by imaging the small intestine, the likelihood of being endoscopic images of the small intestine is determined to be high, and the likelihood of being endoscopic images of the stomach or the large intestine is determined to be low. Thus, the endoscopic images concentrate near coordinates (0,1,0). Basically, as for endoscopic images obtained by imaging the large intestine, the likelihood of being endoscopic images of the large intestine is determined to be high, and the likelihood of being endoscopic images of the stomach or the small intestine is determined to be low. Thus, the endoscopic images concentrate near coordinates (0,0,1). Basically, the likelihood of endoscopic images obtained by imaging the boundary between the stomach and the small intestine and endoscopic images obtained by imaging the boundary between the small intestine and the large intestine being endoscopic images of the stomach, the small intestine, or the large intestine is determined to be low. Thus, the endoscopic images concentrate near coordinates (0,0,0). Therefore, when the number of regions subjected to determination is set to be L, by grouping the endoscopic images into K (≥L+1) clusters, the endoscopic images are expected to be grouped into clusters of endoscopic images for the respective regions sought to be distinguished and other clusters, that is, clusters of candidates images.

As for endoscopic images in which the boundary between the stomach and the small intestine has been captured and endoscopic images in which the boundary between the small intestine and the large intestine has been captured, the likelihood of the former images being endoscopic images of the stomach or the small intestine is determined to be higher than the likelihood of being endoscopic images of the large intestine, and the likelihood of the latter images being endoscopic images of the small intestine or the large intestine is determined to be higher than the likelihood of being endoscopic images of the stomach. Therefore, the former images and the latter images are distributed somewhat away from each other. Therefore, setting the number of clusters such that these images are grouped into different clusters improves the accuracy of clustering. In other words, the plurality of endoscopic images are preferably grouped into K (=2 L−1) clusters, that is, a number of clusters obtained by adding the number of boundaries between the regions to the number of the regions sought to be distinguished.

In an exemplary embodiment, based on information on relative time from the imaging start time of each of a plurality of endoscopic images in addition to the accuracy score of each of the plurality of endoscopic images, that is, based on a vector having each component of the accuracy score and the time information as the vector's components, the grouping unit 52 may group the plurality of endoscopic images into a plurality of clusters by a clustering method. Using the time information for clustering allows endoscopic images having similar time information to be easily grouped into the same cluster, thereby the accuracy of the clustering is improved. Further, for example, as for endoscopic images with time information that are different from each other as in the case of endoscopic images in which the boundary between the stomach and the small intestine has been captured and endoscopic images in which the boundary between the small intestine and the large intestine has been captured, the respective positions of the images are away from each other when time information is used for the clustering. Thus, the accuracy of the clustering becomes improved.

In the following, an explanation will be given by using, as an example, a case where images are grouped into five clusters each surrounded by a dotted line by the grouping unit 52.

For all the clusters, the identification unit 54 identifies a representative vector for each cluster (S14). The representative vector is, for example, the average value or median of the accuracy score (vector) of one or more endoscopic images belonging to the cluster. From among the plurality of clusters, the identification unit 54 identifies clusters into which endoscopic images of the respective regions are highly likely to have been grouped (S16).

More specifically, the identification unit 54 calculates the inner product of the representative vector for each of the plurality of clusters and a standard basis vector (1,0,0) for the stomach and identifies a cluster (hereinafter, also referred to as "stomach cluster") that has the largest inner product as a cluster into which endoscopic images of the stomach are highly likely to have been grouped (S160). In the example in FIG. 4, a cluster 160 located near coordinates (1,0,0) is identified as a stomach cluster. The identification unit 54 calculates the inner product of the representative vector for each of the plurality of clusters and a standard basis vector (0,1,0) for the small intestine and identifies a cluster (hereinafter, also referred to as "small intestine cluster") that has the largest inner product as a cluster into which endoscopic images of the small intestine are highly likely to have been grouped (S162). In the example in FIG. 4, a cluster 162 located near coordinates (0,1,0) is identified as a small intestine cluster. The identification unit 54 calculates the inner product of the representative vector for each of the plurality of clusters and a standard basis vector (0,0,1) for the large intestine and identifies a cluster (hereinafter, also referred to as "large intestine cluster") that has the largest inner product as a cluster into which endoscopic images of the large intestine are highly likely to have been grouped (S164). In the example in FIG. 4, a cluster 164 located near coordinates (0,0,1) is identified as a large intestine cluster.

The identification unit 54 identifies clusters other than the stomach cluster, the small intestine cluster, and the large intestine cluster as clusters (hereinafter, also referred to as "boundary clusters") into which images of the boundaries between the regions are highly likely to have been grouped (S18). In the example in FIG. 4, clusters 166 and 168 located near coordinates (0,0,0) are identified as boundary clusters. The identification unit 54 identifies, as candidate images, endoscopic images grouped into the boundary clusters (S20). In addition to the endoscopic images grouped into the boundary clusters, the identification unit 54 may identify, as candidate images, endoscopic images whose imaging time is sandwiched between those of two arbitrary endoscopic images grouped into the boundary clusters from among endoscopic images grouped into other clusters. The identification unit 54 provides the respective image IDs of the identified candidate images to the compression processing unit 40.

<Compression Process on Endoscope RAW Images>

An image analysis process performed by the redness determination unit 34, the image summarization processing unit 36, and the candidate image identification unit 38 is performed at the time of a compression process on endoscopic RAW images performed by the compression processing unit 40. The compression processing unit 40 performs a lossy compression process on an endoscopic RAW image so as to generate an image file to which an image ID and imaging time information are added and records the image file in the endoscopic image recording unit 60. For example, the compression processing unit 40 may compress an endoscopic RAW image in an image format such as JPEG.

To a compressed image file, the compression processing unit 40 adds information indicating analysis results provided from the redness determination unit 34, the image summarization processing unit 36, and the candidate image identification unit 38. More specifically, to the compressed image having an image ID provided from the redness determination unit 34, the compression processing unit 40 adds information indicating that the image is a reddish image. This information may be added as flag information. Based on the result of the image summarization process performed by the image summarization processing unit 36, the compression processing unit 40 adds, to a reference image, flag information showing that the image is a reference image and adds, to a similar image, flag information showing that the image is a similar image. Whether an image is a reference image or a similar image is in a front/back relationship. Thus, a flag value 1 may represent a reference image, and a flag value 0 may represent a similar image. Further, to a compressed image having an image ID provided from the candidate image identification unit 38, the compression processing unit 40 adds information indicating that the image is a candidate image.

In an exemplary embodiment, the redness determination unit 34, the image summarization processing unit 36, and the candidate image identification unit 38 each performs an image process on an endoscopic RAW image before the compression process on the endoscopic RAW image is performed by the compression processing unit 40. In an exemplary variation, the redness determination unit 34, the image summarization processing unit 36, and the candidate image identification unit 38 may each perform image analysis on a compressed image, and information indicating the analysis results to the compressed image. The endoscopic image recording unit 60 records an image file on which the image process has been performed by the image processing unit 32, and the user observes an endoscopic image using the image file recorded in the endoscopic image recording unit 60.

A screen that is displayed on the display device 22 at the time of image interpretation will be described in the following. A doctor B, who is the user, enters the user ID and the password into a terminal device 20 so as to log in. When the user logs in, the management server 10 supplies examination information recorded in the examination information recording unit 62, and the display device 22 displays a list of capsule endoscopic examinations. An examination list screen displays examination information such as the patient ID, the patient name, the examination ID, the date and time of the examination, and the user selects an examination for which an image interpretation report is to be created. When an examination with an examination ID "1111", a patient name "A", and an examination ID "0001" is selected from the list of examinations, the display control unit 42 generates an image interpretation screen for interpreting an endoscopic image and causes the display device 22 to display the image interpretation screen.

Figure 5:
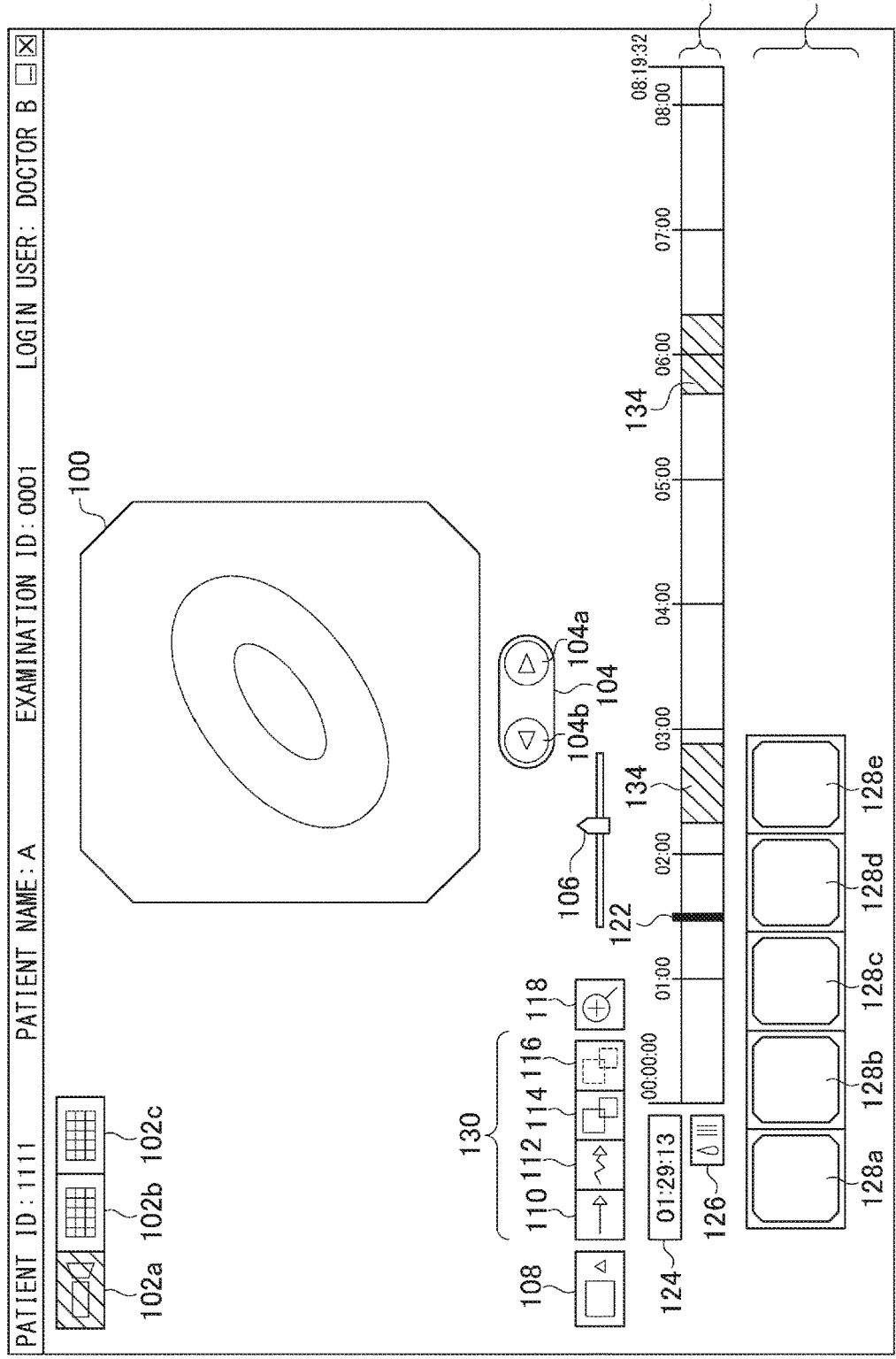
FIG. 5 is a diagram showing an example of an image interpretation screen for an endoscopic image.

FIG. 5 shows an example of an image interpretation screen for an endoscopic image. A playback area 100 for switching endoscopic images so as to play back and display the endoscopic images is provided at the upper center part of the image interpretation screen. The image interpretation screen is displayed on the display device 22 in a state where a playback mode selection button 102a located at the upper left corner of the screen is being selected. When an overview mode selection button 102b is selected, the display control unit 42 generates an overview screen shown in FIG. 6 and displays the overview screen on the display device 22. When a candidate image selection button is selected, the display control unit 42 generates a candidate image selection screen shown in FIG. 7 and displays the candidate image selection screen on the display device 22.

A playback number switching button 108 is an operation button for switching the number of images displayed in the playback area 100. Although FIG. 5 shows an example where one-image display is selected, the user can select two-image display or four-image display by operating the playback number switching button 108.

A second playback mode selection button 110 is an operation button for selecting the second playback mode. A third playback mode selection button 112 is an operation button for selecting the third playback mode. A fourth playback mode selection button 114 is an operation button for selecting the fourth playback mode where only reference images are played back and displayed. A secondary fourth playback mode selection button 116 is an operation button for selecting the secondary fourth playback mode where only similar images are played back and displayed. In the fourth playback mode, since the playback display of similar images is omitted, the user is recommended to observe all the endoscopic images by also performing image interpretation in the secondary fourth playback mode when the user selects the fourth playback mode so as to perform image interpretation.

The user selects one of the second playback mode selection button 110, the third playback mode selection button 112, the fourth playback mode selection button 114, and the secondary fourth playback mode selection button 116 so as to set the playback mode. Under the default state, the second playback mode selection button 110 is selected. A playback button 104*a* and a reverse playback button 104*b* are displayed in a playback button display area 104 provided below the playback area 100. When the playback button 104*a* is selected, endoscopic images are displayed in the forward direction (the direction moving from an image with an old imaging time toward a new image) in the playback area 100. When the reverse playback button 104*b* is selected, the endoscopic images are displayed in the backward direction (the direction moving from an image with a new imaging time toward an old image) in the playback area 100. A playback speed adjustment unit 106 includes a slider for adjusting the playback speed (display time for one endoscopic image). The playback speed adjustment unit 106 sets the playback speed, that is, the display frame rate of the endoscopic images, according to the position of the slider. For example, the display frame rate of 20 fps means that 20 endoscopic images are switched and displayed per second, and the display time per one image is 0.05 seconds.

The playback processing unit 46 plays back and displays the endoscope images in the playback area 100 according to the playback mode selected in a playback mode selection area 130 and the playback speed (display frame rate) set by the playback speed adjustment unit 106. When the playback button 104*a* or the reverse playback button 104*b* is selected, the playback processing unit 46 starts playing back and displays the images, and a pause button is displayed instead at the place of the playback button 104*a* or the reverse playback button 104*b*. When the user operates the pause button during the playing back and displaying of the endoscopic images, the playback processing unit 46 pauses the playing back and displaying of the endoscopic images. When the user operates the mouse wheel in this state, the playback processing unit 46 displays the endoscopic images frame-by-frame in the first playback mode in accordance with the rotation of the mouse wheel.

When the user places the mouse pointer on an image displayed in the playback area 100 and double-clicks the left button of the mouse, the image is captured and displayed in a captured image display area 128. The captured image displayed in the captured image display area 128 may be selected as an image attached to an image interpretation report later. This example shows a state where eight captured images 128*a* through 128*h* are selected.

Below the playback area 100, the display control unit 42 displays a time bar 120 with one end indicating the imaging start time and the other end indicating the imaging end time. In the embodiment, the time bar 120 is a laterally elongated rectangular bar with the left end indicating the imaging start time and the right end indicating the imaging end time, and a slider 122 shows the temporal position of an endoscopic image displayed in the playback area 100. A time position expressed by the slider 122 is also displayed in a time display area 124 as information on relative time from the imaging start time. When the user places the mouse pointer on an arbitrary position of the time bar 120 and clicks the left button of the mouse, an endoscope image at that time position is displayed in the playback area 100. Even when the user drags the slider 122 and drops the slider 122 at an arbitrary position in the time bar 120, an endoscope image at that time position is displayed in the playback area 100.

The display control unit 42 displays the average color value of an endoscope image in the time bar 120. The display control unit 42 calculates the average color value of each endoscopic image and colors the inside of the rectangular area of the time bar 120 according to the average color value of each endoscope image at a position corresponding to the time position of the endoscopic image. As a result, the time bar 120 is displayed as a color bar expressing the temporal color tone of an endoscope image. Since the color tone of an endoscopic image imaged by the capsule endoscope 3 varies depending on the thickness of the imaged digestive tract or the like, adding a color based on an image average color value to the time bar 120 by the display control unit 42 allows the image interpreter to sensuously perceive the relationship between the imaging time and the imaged section.

The display control unit 42 further displays an indicator 134 indicating the imaging time of a candidate image in the time bar 120. In FIG. 5, the indicator 134 is displayed as shading on the time bar 120. However, the indicator 134 may be colored using a predetermined color. By displaying the indicator 134, the user can recognize the existence of an image in which a candidate image is highly likely to have been captured. When a landmark is set as described later, the display control unit 42 may change the display mode of the indicator 134 to be different from that before the setting of the landmark. After the landmark is set, the display control unit 42 may hide the indicator 134 since there is no need to present information on the candidate image to the user.

A red image display button 126 is a button for displaying a red mark for the imaging time of a reddish image in the time bar 120. When the red image display button 126 is operated, the display control unit 42 displays a red mark for the imaging time of a reddish image. By displaying the red mark on the time bar 120, the user can recognize the presence of an image in which bleeding is highly likely to have been captured.

An enlargement display button 118 is a button for enlarging the playback area 100. When the enlargement display button 118 is operated, the captured image display area 128 is not displayed, and the playback area 100 is enlarged correspondingly.

The user can add a mark for indicating the start position of a region to the time bar 120. This addition of a mark is also called the setting of a landmark (or landmarks) and is carried out in order to identify the range of a region in a captured image for the purpose of improving the efficiency of image diagnosis. The user starts playback display from the time position at the left end of the indicator 134 or a time position that is slightly before the time position by the operation of the mouse. When an image of a new region is played back while the user is observing an endoscopic image played back and displayed in the playback area 100, the user stops the playback display of the playback area 100, places the mouse pointer on a boundary image displayed in the playback area 100, and right clicks the mouse. The display control unit 42 displays a selection window that includes options for the setting of landmarks. Three items for setting landmarks for the respective start positions of the stomach, the small intestine, and the large intestine are displayed in the selection window. By selecting an item, the user can set a landmark for the starting position of a region identified by the item in the time bar 120. The landmark is displayed in the time bar 120 in such a manner that the image interpreter can recognize the boundary. By setting landmarks, the image interpreter can easily know the start position of a region when reviewing endoscope images.

When the overview mode selection button 102*b* located at the upper left corner of the screen is selected, the display control unit 42 generates an overview screen and displays the overview screen on the display device 22. On the overview screen, images extracted from a plurality of reference images identified through the image summarization process are displayed.

Figure 6:
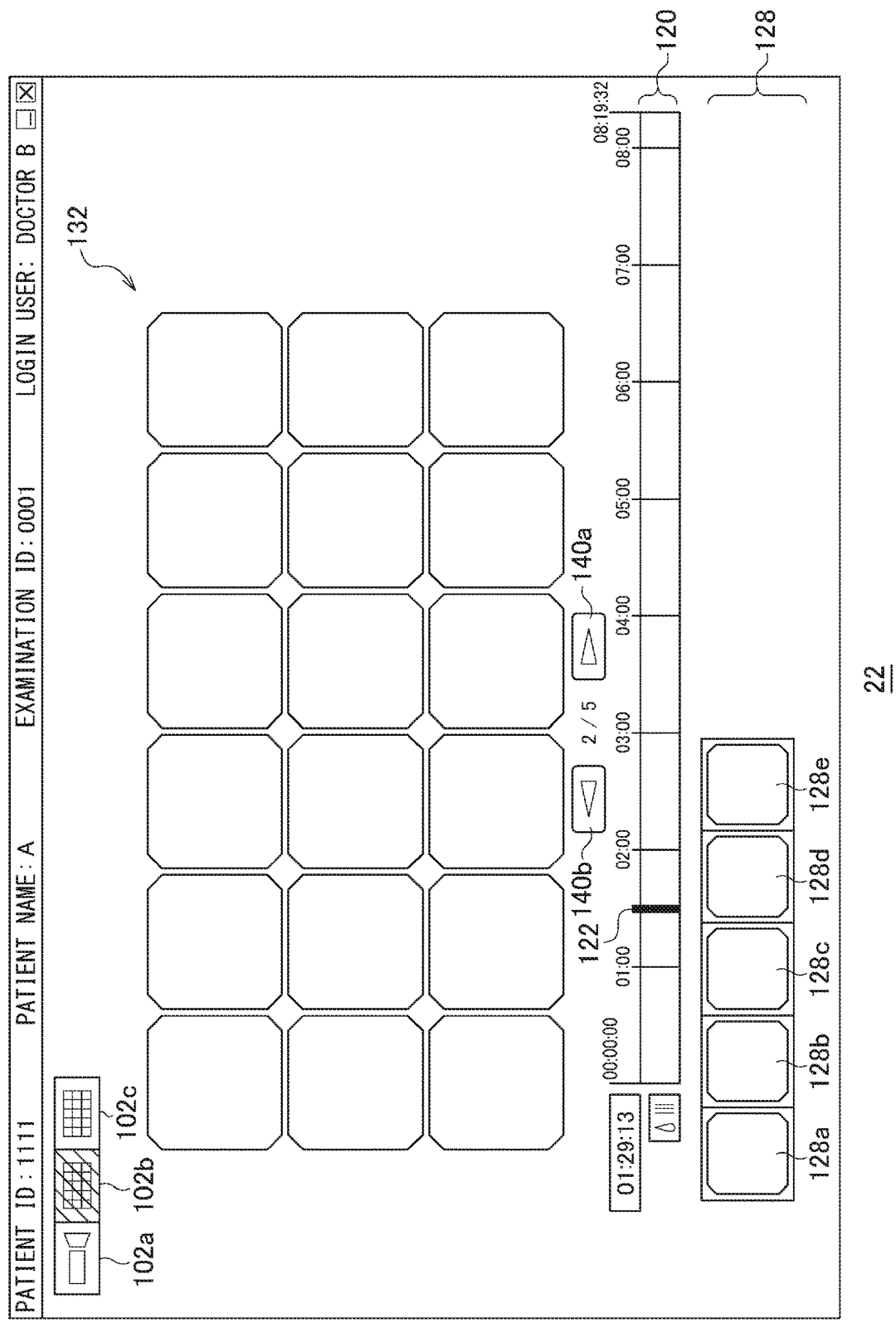
FIG. 6 is a diagram showing an example of an overview screen for endoscopic images.

FIG. 6 shows an example of the overview screen for endoscopic images. In an image display area 132, images extracted from a plurality of reference images are displayed while being arranged in a lattice pattern. For example, when 20,000 or so reference images are identified from 60,000 or so endoscopic images, the display control unit 42 displays images extracted at predetermined intervals from the 20,000 or so reference images on the overview screen. The number of images to be extracted may be freely set by the user with an upper limit of 2,000 images. Given that the number of the reference images is N and the number of the images to be included in the overview screen is M, the display control unit 42 extracts an image every (N/M) images out of the reference images arranged in a time-series manner. For example, when N equals to 20,000 images and M equals to 2,000 images, the display control unit 42 extracts one reference image every 10 images in the order of imaging time and arranges the reference image on the overview screen. Extracted images are arranged in a lattice pattern in the image display area 132, and the user can switch images by operating page feeding buttons 140a and 140b. Since endoscopic images displayed on the overview screen are reference images and are limited to those that are dissimilar to each other, the user can understand the outline of the entire examination efficiently.

FIG. 5 is referred back. When a candidate image list selection button 102c at the upper left corner of the screen is selected, the display control unit 42 identifies, in reference to additional information, candidate images in which the boundary of a region in the body may have been captured from among the plurality of reference images, generates a candidate image list display screen including the candidate images, and displays the candidate image list display screen on the display device 22. When the mouse pointer is placed on the indicator 134 displayed on the time bar 120 and the mouse is right-clicked, the display control unit 42 may display a selection window including an option for selecting "display candidate screen list screen" and generate a candidate image list screen when the option is selected so as to display the candidate image list screen on the display device 22.

Figure 7:
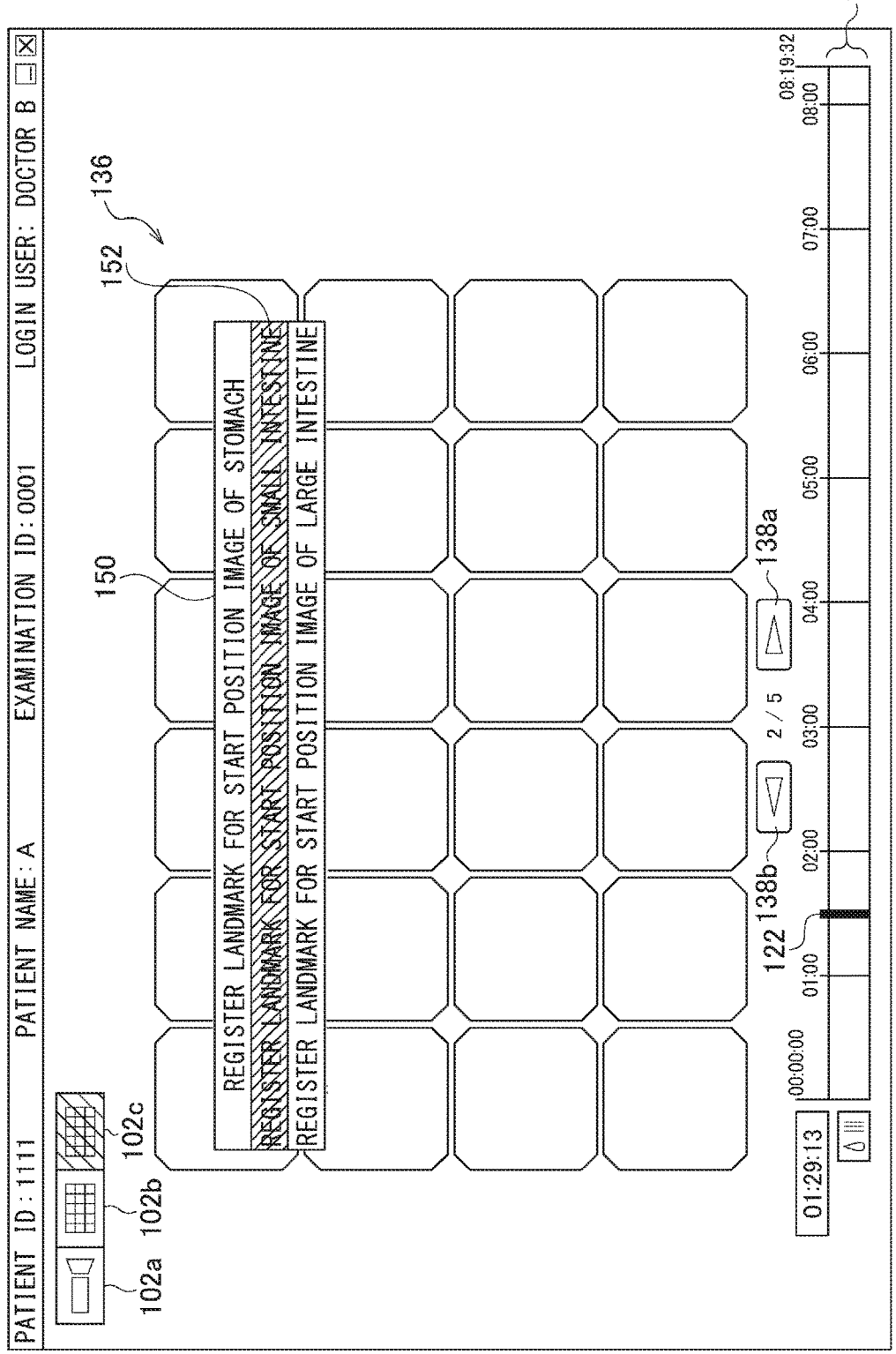
FIG. 7 is a diagram showing an example of a candidate image list screen.

FIG. 7 shows an example of the candidate image list screen. The image display area 136 displays a list of candidate images arranged in a lattice pattern. The user can switch images by operating page feeding buttons 138a and 138b. When the user double-clicks a candidate image with the mouse, the candidate image is enlarged and displayed. Since the candidate images are displayed in a list, the boundary of a region in the body can be easily found.

When the user confirms that the candidate image is an image in which the entrance of the small intestine has been captured, the user places the mouse pointer on the candidate image and right clicks the mouse. The display control unit 42 displays a selection window 150 that includes options for the setting of landmarks. Three items for setting landmarks for the respective start positions of the stomach, the small intestine, and the large intestine are displayed in the selection window 150. By moving a selection frame 152 to a desired item and performing a determination operation (e.g., double-clicking of the mouse), the user can set a landmark for the candidate image as a start position image of the region in the body. The image ID of the image to which the landmark has been set is recorded as the image ID of a landmark image in the observation detail recording unit 64, and a mark indicating the start position of the small intestine is added to the imaging position of the candidate image on the time bar 120. After setting landmarks on the candidate image list screen shown in FIG. 7 first, the user may perform image observation on the interpretation screen shown in FIG. 4 or the overview screen shown in FIG. 5.

Figure 8:
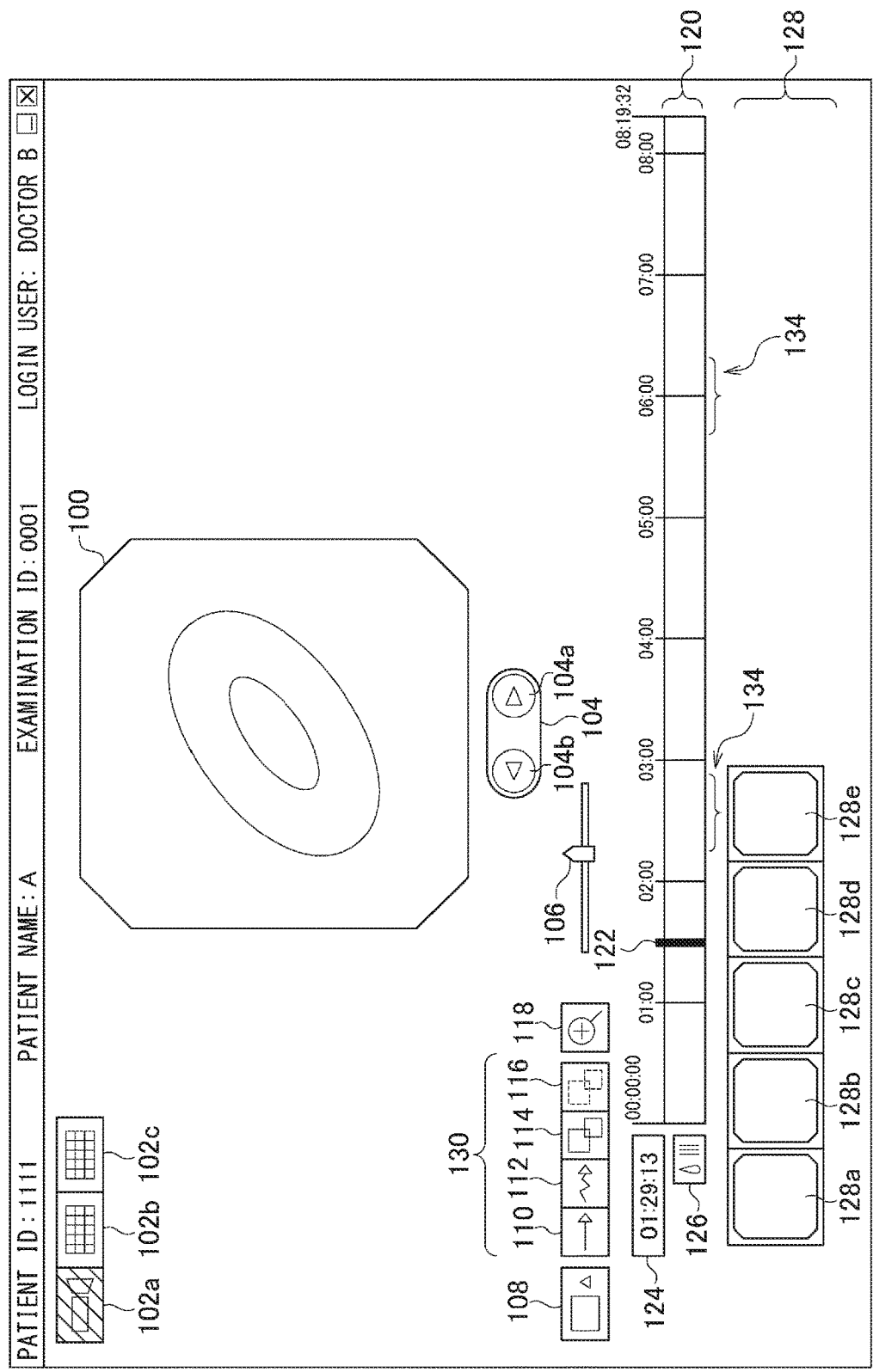
FIG. 8 is a diagram showing another example of an image interpretation screen for an endoscopic image.

FIG. 8 shows another example of an image interpretation screen for an endoscopic image. The display control unit 42 displays, using curly brackets, indicators 134 indicating the imaging time of candidate images under the time bar 120. By displaying the curly bracket indicators 134, the user can recognize the range of images in which the candidate images are highly likely to have been captured.

Figure 9:
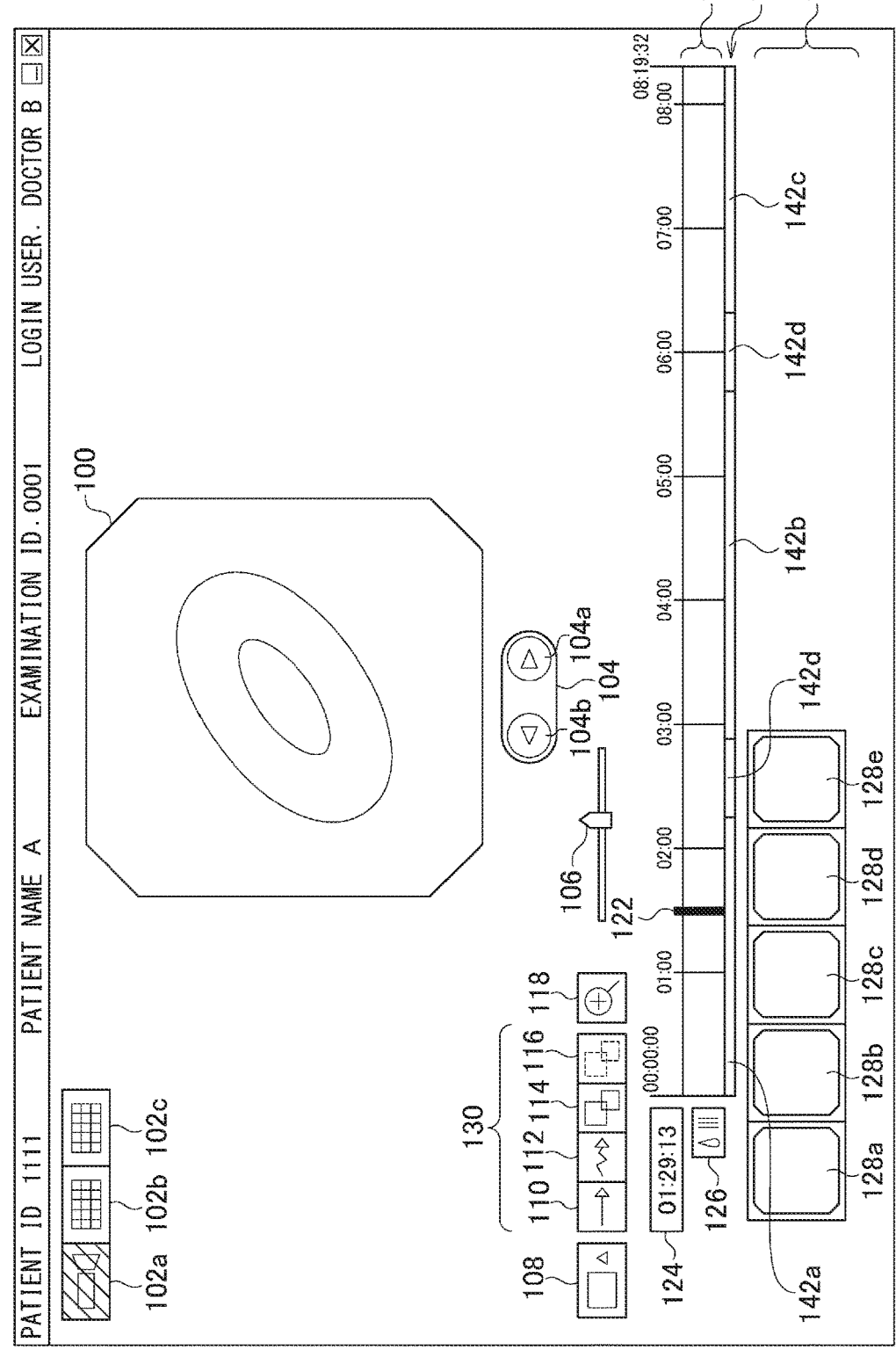
FIG. 9 is a diagram showing yet another example of an image interpretation screen for an endoscopic image.

FIG. 9 shows yet another example of an image interpretation screen for an endoscopic image. Under the time bar 120, the display control unit 42 displays a region bar 142 adjacent to the time bar 120. The region bar 142 is a horizontally long rectangular bar having the same length as that of the time bar 120 and is displayed in such a manner that whether an endoscopic image displayed in the playback area 100 is an endoscopic image of each of the regions: the stomach; the small intestine; and the large intestine or is a candidate image can be identified. For example, in the region bar 142, a section 142a corresponding to the stomach, a section 142b corresponding to the small intestine, a section 142c corresponding to the large intestine, and a section 142d corresponding to the boundary may be displayed in different colors.

According to the endoscopic image observation system 1 according to the first embodiment described above, by clustering the accuracy score, the range in which the boundary of a region is to be searched for is identified. This allows the image interpreter to easily find the boundary of the region.

Second Embodiment

Figure 10:
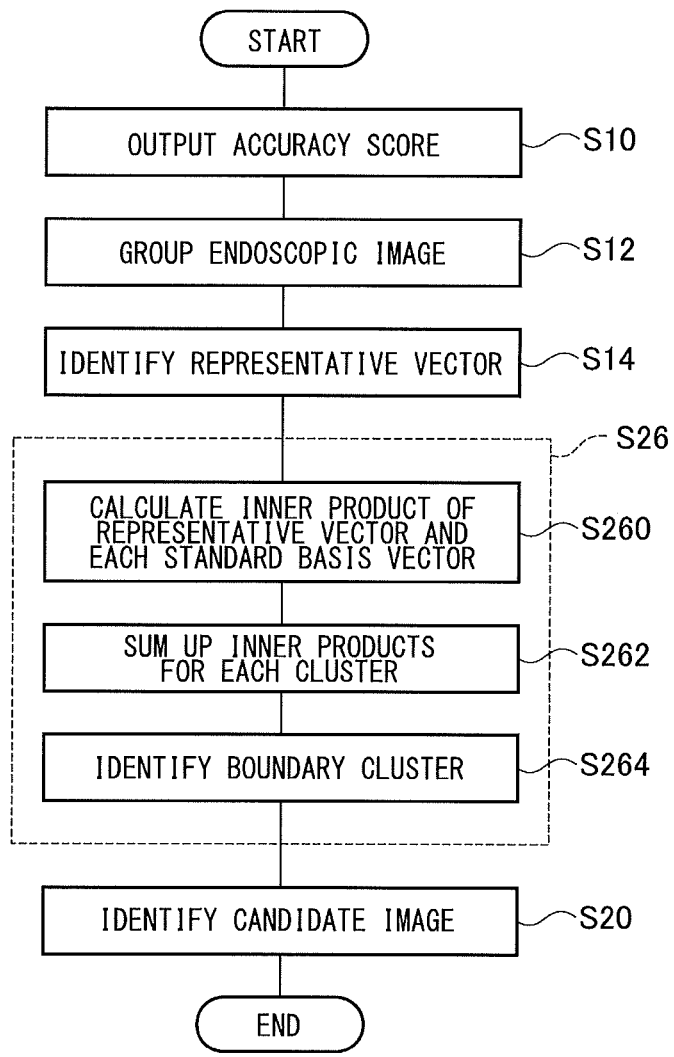
FIG. 10 is a diagram showing a flowchart of a candidate image identification process according to a second embodiment.

FIG. 10 shows a flowchart of a candidate image identification process. FIG. 10 corresponds to FIG. 3 in the first embodiment. The main difference from the endoscopic image observation system 1 according to the first embodiment is a process performed by the candidate image identification unit 38. Differences from the endoscopic image observation system 1 according to the first embodiment will be mainly described in the following.

Since the steps through S14 are the same as those in FIG. 3, an explanation will be made starting from S26. From among the plurality of clusters, the identification unit 54 identifies boundary clusters (S26). More specifically, the identification unit 54 calculates the inner product of the representative vector for each of the plurality of clusters and each standard basis vector (S260) and sums up the inner products for each cluster (S262). The identification unit 54 identifies, as the boundary clusters, clusters obtained by excluding (K-N) clusters, that is, the number of clusters corresponding to the regions subjected to determination in ascending order of the sum of the inner products (S264). The identification unit 54 identifies, as candidate images, endoscopic images grouped into the clusters (S20).

According to the endoscopic image observation system according to the second embodiment described above, the same effects as those by the endoscopic image observation system 1 according to the first embodiment can be achieved.

Third Embodiment

Figure 11:
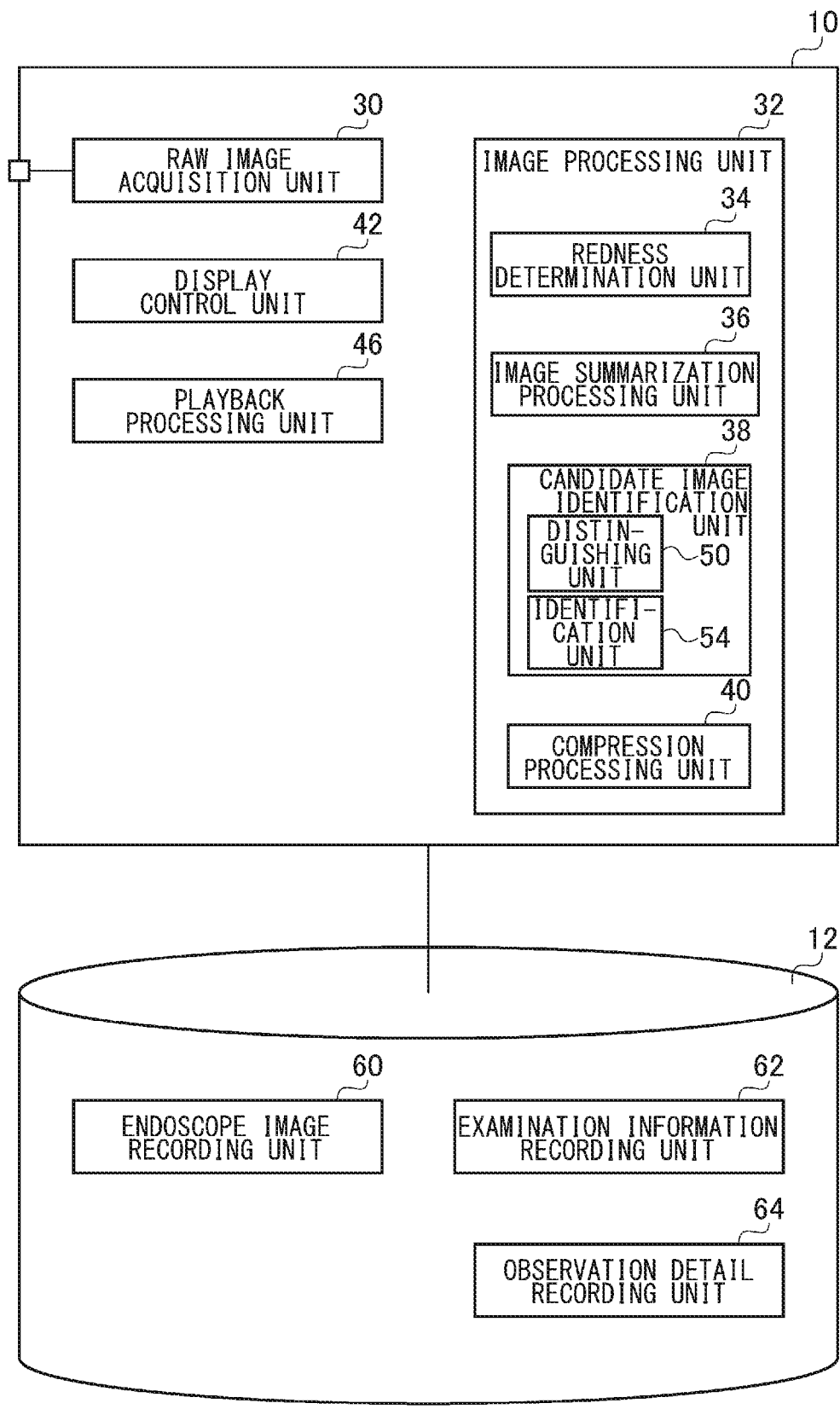
FIG. 11 is a diagram showing the configuration of a management server and a recorder of an endoscopic image observation system according to a third embodiment.

FIG. 11 shows the configuration of a management server 10 and a recorder 12 of an endoscopic image observation system according to a third embodiment. FIG. 11 corresponds to FIG. 2 in the first embodiment. The main difference from the endoscopic image observation system 1 according to the first embodiment is a process performed by the candidate image identification unit 38. Differences from the endoscopic image observation system 1 according to the first embodiment will be mainly described in the following.

The management server 10 includes a RAW image acquisition unit 30, an image processing unit 32, a display control unit 42, and a playback processing unit 46. The image processing unit 32 has a redness determination unit 34, an image summarization processing unit 36, a candidate image identification unit 38, and a compression processing unit 40. The candidate image identification unit 38 has a distinguishing unit 50 and an identification unit 54.

In the present embodiment, regarding the likelihood that each endoscopic image represents an endoscopic image of each region sought to be distinguished, the distinguishing unit 50 outputs the likelihood for a region with the highest likelihood as an accuracy score. In the same way as in the first embodiment, the distinguishing unit 50 may output a vector having the likelihood of being an endoscopic image of each region as a component and output the absolute value thereof as the accuracy score. In any case, the distinguishing unit 50 outputs the accuracy score in a scalar quantity.

The identification unit 54 identifies an endoscopic image having a relatively low accuracy score, specifically, an endoscopic image whose accuracy score is lower than a predetermined threshold (0<threshold value<1) as a candidate image. For the threshold value, it is only necessary to set a value that allows the candidate image to be accurately identified based on experiments and various findings.

In an exemplary variation, the identification unit 54 may identify, as a candidate image, an endoscopic image that is in an area other than the area in which a predetermined number of images exceed the threshold value in succession.

According to the endoscopic image observation system according to the third embodiment described above, the same effects as those by the endoscopic image observation system 1 according to the first embodiment can be achieved.

Described above is an explanation of the present invention based on the embodiments. These embodiments are intended to be illustrative only, and it will be obvious to those skilled in the art that various modifications to constituting elements and processes could be developed and that such modifications are also within the scope of the present invention.

(First Exemplary Variation)

Figure 12:
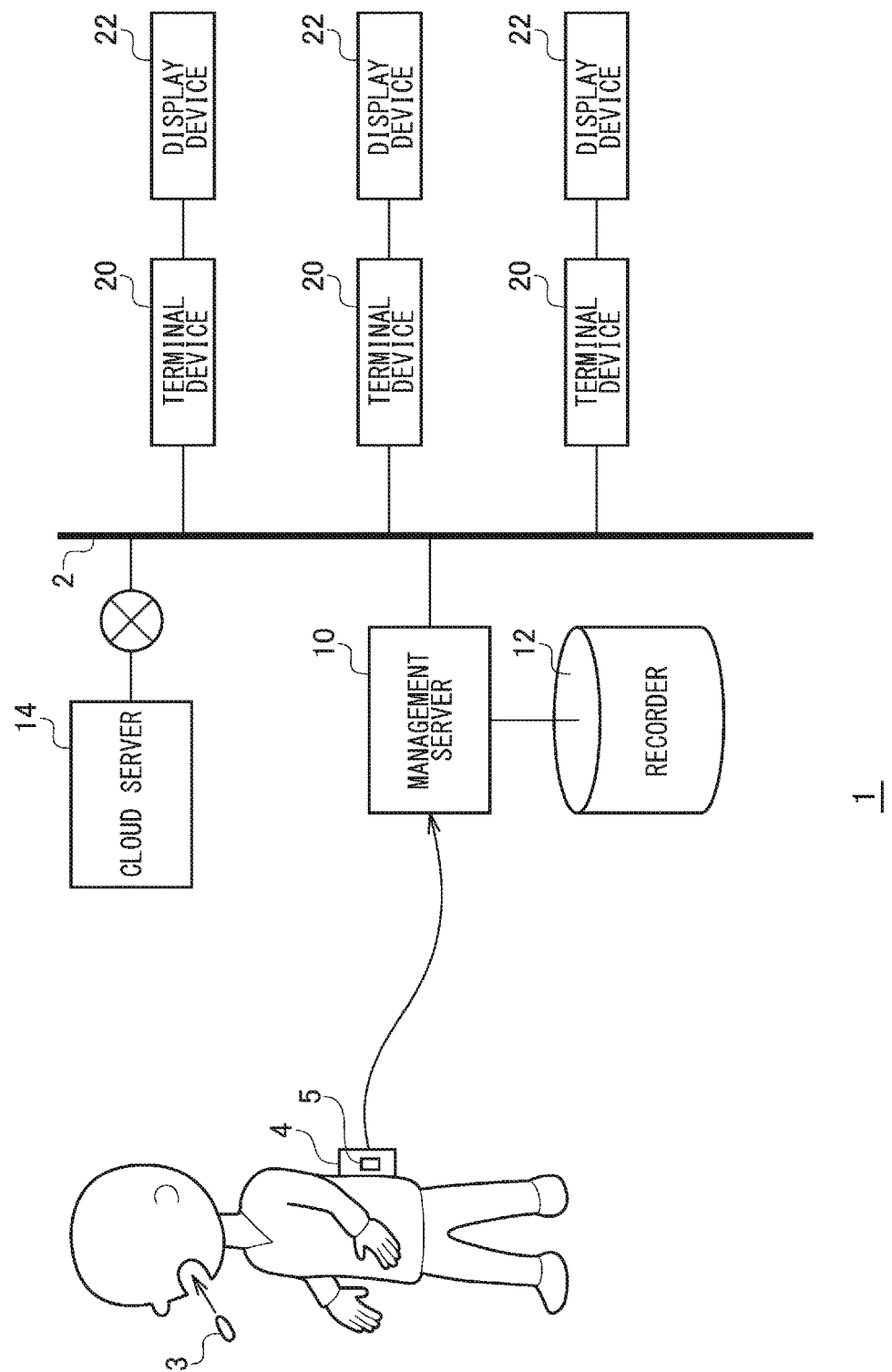
FIG. 12 is a diagram for explaining the outline of an endoscopic image observation system according to an exemplary variation.

FIG. 12 is a diagram for explaining the outline of an endoscopic image observation system according to an exemplary variation. FIG. 12 corresponds to FIG. 1 in the first embodiment. In this exemplary variation, an endoscopic image observation system 1 further includes a cloud server 14. The cloud server 14 is a server provided by a cloud service provider.

Figure 13:
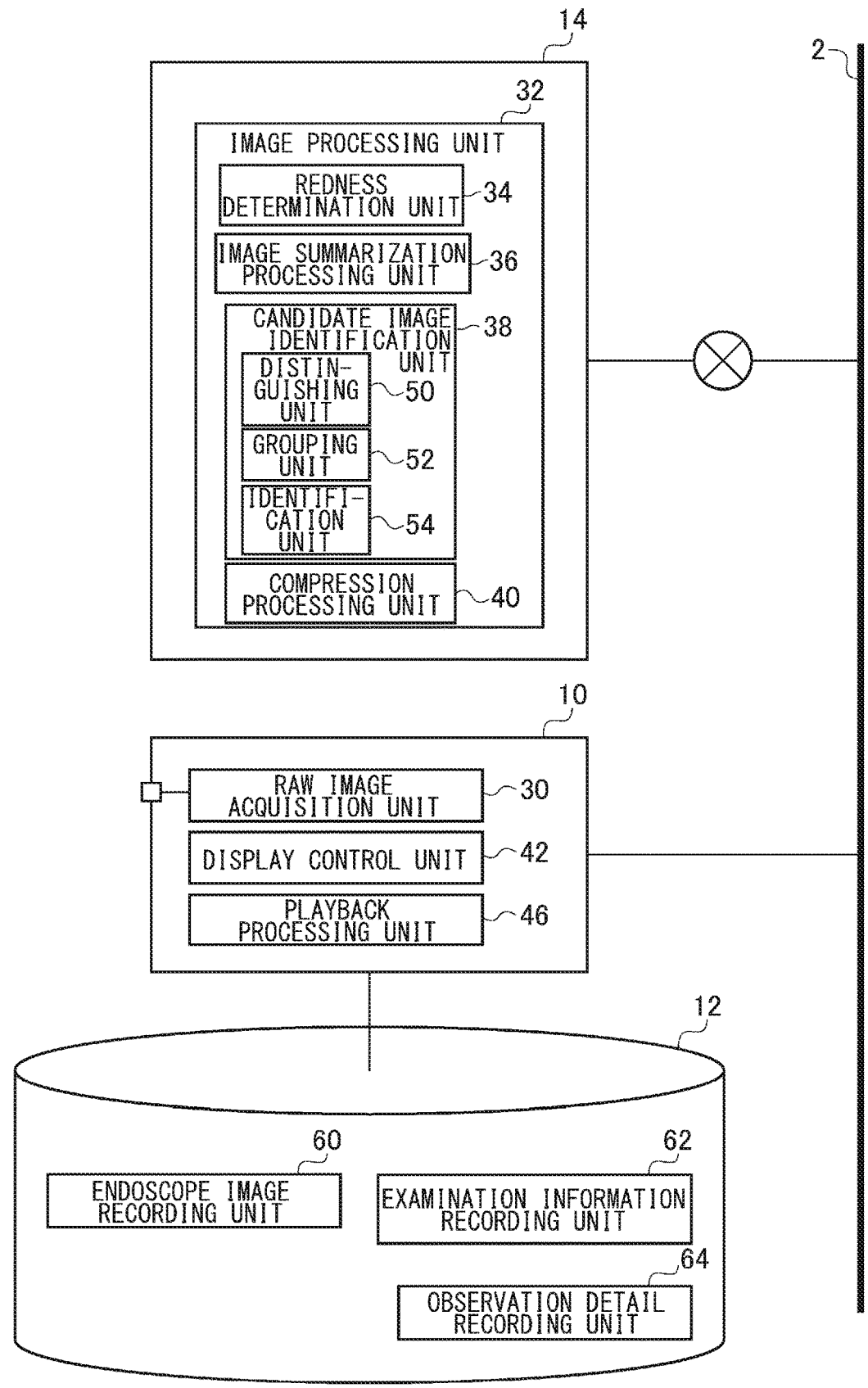
FIG. 13 is a diagram showing the configuration of a management server, a recorder, and a cloud server of FIG. 12.

FIG. 13 is a diagram showing the configuration of a management server 10, a recorder 12, and a cloud server 14. FIG. 13 corresponds to FIG. 1 in the first embodiment. The management server 10 includes a RAW image acquisition unit 30, a display control unit 42, and a playback processing unit 46. The cloud server 14 includes an image processing unit 32. That is, in this exemplary variation, the management server 10 does not have the function of the image processing unit 32, and the cloud server 14 has the function of the image processing unit 32 instead. The image processing unit 32 of the cloud server 14 performs the identification of reddish images, an image summarization process, and the identification of boundary candidate images on the endoscopic RAW images temporarily stored in the recorder 12. The compression processing unit 40 generates an image file to which predetermined information is added and transmits the image file to the recorder 12 so as to record the image file in the endoscopic image recording unit 60.

(Second Exemplary Variation)

Figure 14:
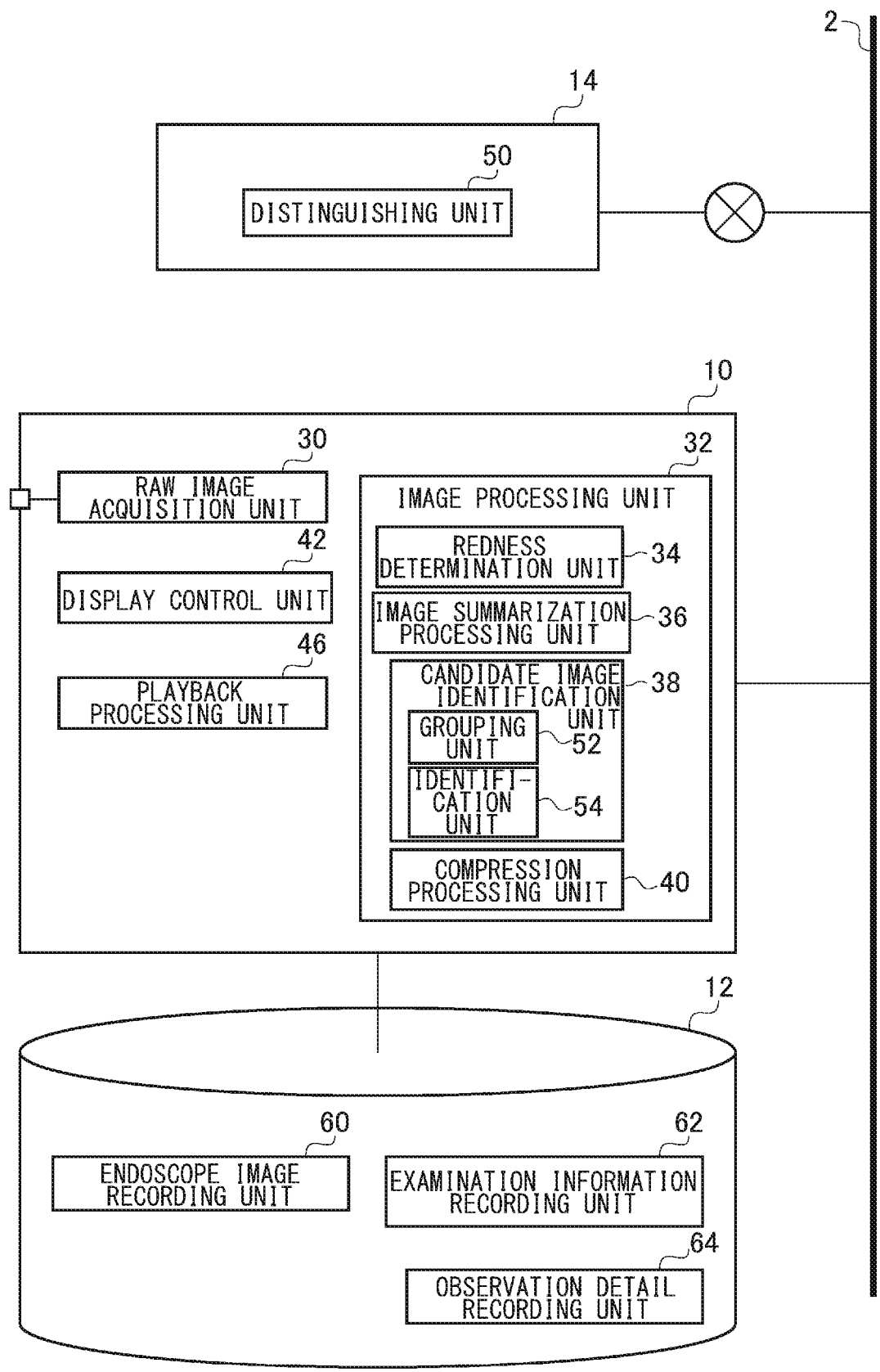
FIG. 14 is a diagram showing the configuration of a management server, a recorder, and a cloud server of an endoscopic image observation system according to another exemplary variation.

In the first exemplary variation, a case where the cloud server 14 has all the functions of the candidate image identification unit 38 has been described. The cloud server 14 may have only some of the functions of the candidate image identification unit 38. FIG. 14 is a diagram showing the configuration of a management server 10, a recorder 12, and a cloud server 14 of an endoscopic image observation system according to another exemplary variation. The candidate image identification unit 38 of the image processing unit 32 of the management server 10 has a grouping unit 52 and an identification unit 54. The cloud server 14 has a distinguishing unit 50. That is, in this exemplary variation, the candidate image identification unit 38 of the image processing unit 32 of the management server 10 does not have the function of the distinguishing unit 50, and the cloud server 14 has the function of the distinguishing unit 50 instead. The distinguishing unit 50 performs a process of outputting an accuracy score on the endoscopic RAW images temporarily stored in the recorder 12. The distinguishing unit 50 provides the candidate image identification unit 38 of the management server 10 with the accuracy score that has been output.

What is claimed is:

1. An endoscopic image observation system for supporting observation of a plurality of images captured by an endoscope comprising a processor comprising hardware, wherein the processor is configured to:
    output an accuracy score indicating a likelihood that each of the plurality of images represents an image of a site sought to be distinguished;
    group the plurality of images into a plurality of clusters in accordance with the accuracy score; and
    identify a candidate image for a boundary of the site from among the plurality of images in accordance with the grouping into the plurality of clusters,
    wherein, when there are a plurality of sites sought to be distinguished, the processor is configured to:
        output as an accuracy score a vector including the likelihood that each of the plurality of images represents an image of each of the plurality of sites sought to be distinguished as a component;
        identify a representative vector representing the accuracy score of one or more grouped images for each of the plurality of clusters; and
        identify, from among the plurality of clusters, a predetermined number of clusters in ascending order of the sum of the respective inner products of the representative vector and respective standard basis vector for the plurality of sites sought to be distinguished, as a cluster into which the candidate image is grouped.

2. The endoscopic image observation system according to claim 1,
    wherein given that the number of sites sought to be distinguished is L, the processor is configured to group the plurality of images into (L+1) clusters or more.

3. The endoscopic image observation system according to claim 1, wherein the vector further includes information on relative time from an imaging start time of each of the plurality of images as a component.

4. The endoscopic image observation system according to claim 1,
wherein the processor is configured to output an accuracy score indicating the likelihood that each of the plurality of images represents at least any one of images of a stomach, a small intestine, and a large intestine.

5. The endoscopic image observation system according to claim 1,
wherein the processor is configured to display information regarding the candidate image on a display.

6. The endoscopic image observation system according to claim 5,
wherein the processor is configured to display the candidate image on a display in a list.

7. The endoscopic image observation system according to claim 5,
wherein the processor is configured to display a time bar with one end indicating the imaging start time and the other end indicating the imaging end time and also display an indicator for a candidate image in association with the time bar.

8. The endoscopic image observation system according to claim 5,
wherein the processor is configured to display a bar displaying that an image at each imaging time is an image of a predetermined site or the candidate image in association with the imaging time of the image.

* * * * *